United States Patent
Uchihara et al.

(10) Patent No.: US 8,682,099 B2
(45) Date of Patent: Mar. 25, 2014

(54) IMAGE CORRECTION METHOD AND IMAGE CORRECTION DEVICE

(75) Inventors: Masanobu Uchihara, Kanagawa (JP); Takao Kuwabara, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 846 days.

(21) Appl. No.: 12/662,069

(22) Filed: Mar. 30, 2010

(65) Prior Publication Data
US 2010/0246922 A1 Sep. 30, 2010

(30) Foreign Application Priority Data
Mar. 31, 2009 (JP) ................. 2009-086496

(51) Int. Cl.
*G06K 9/40* (2006.01)
*G06T 5/00* (2006.01)

(52) U.S. Cl.
CPC ....... *G06T 5/001* (2013.01); *G06T 2207/10116* (2013.01); *G06T 2207/10124* (2013.01)
USPC ............ 382/275; 382/266; 382/132; 382/264

(58) Field of Classification Search
None
See application file for complete search history.

(56) References Cited

U.S. PATENT DOCUMENTS 5,802,135 A * 9/1998 Wohlrab ........................... 378/4
2003/0091243 A1 5/2003 Sasada

FOREIGN PATENT DOCUMENTS

JP 2003-150954 5/2003

OTHER PUBLICATIONS

Patrenahalli Narendra, A Separable Median Filter for Image Noise Smoothing, IEEE 1981.*

* cited by examiner

*Primary Examiner* — Chan Park
*Assistant Examiner* — Mark Roz
(74) *Attorney, Agent, or Firm* — Jean C. Edwards, Esq.; Edwards Neils PLLC (57) ABSTRACT

An image correction method comprises the steps of: median-processing the original image in a direction normal to a direction in which the streak unevenness extends to produce a median-processed image, subtracting the median-processed image from the original image to produce a subtraction image, threshold-processing a part of the subtraction image having a density exceeding a given threshold to reduce the density and produce a threshold-processed image, frequency-processing the threshold-processed image using a one-dimensional low-pass filter in the direction in which the streak unevenness extends to produce a processing image, and subtracting the processing image from the original image to remove the streak unevenness from the original image.

14 Claims, 5 Drawing Sheets

IMAGE CORRECTION METHOD AND IMAGE CORRECTION DEVICE

CROSS-REFERENCE TO RELATED APPLICATIONS

The present application claims priority from Japanese Patent Application No. 2009-086496, filed Mar. 31, 2009, the contents of which are herein incorporated by reference in their entirety.

BACKGROUND OF THE INVENTION

The present invention relates to correction of streak unevenness that has developed in an image and particularly to an image correction method and an image correction device capable of restricting occurrence of ringing and preventing removal of a necessary subject to achieve correction of streak unevenness.

A radiographic image detector has been conventionally used to produce diagnostic images in medicine or to conduct nondestructive tests in industry. The radiographic image detector converts radiation that has penetrated a subject into an electric signal to achieve radiographic imaging. The radiation here includes X-ray, α-ray, β-ray, γ-ray, electron beam, and ultraviolet ray.

Among known radiographic image detectors is a so-called flat panel detector (referred to as FPD below) that extracts an electric image signal from radiation.

There are two types of FPDs: a direct type and an indirect type. The direct type of FPD collects and reads out electron-hole pairs generated by a photoconductive film such as one formed of amorphous selenium in response to incident radiation, as an electric signal. Thus, the direct type directly converts radiation into an electric signal. The indirect type has a phosphor layer or a scintillator layer formed of a phosphor that emits light or fluoresces in response to incident radiation to convert radiation into visible light through that phosphor layer, reading out the visible light with a photoelectric transducer. Thus, the indirect type converts radiation into visible light and then the visible light into an electric signal.

There is also known an apparatus using, in lieu of an FPD, a radiographic image conversion panel or an imaging plate (IP) having a film formed of photostimulable phosphor that accumulates a part of the radiation energy in response to irradiation and emits photostimulable light corresponding to the accumulated energy in response to subsequent irradiation with an excitation light such as visible light. An example of such an apparatus in practical use is an FCR or Fuji Computed Radiography provided by FUJIFILM Corporation.

Where an FPD is used, linear unevenness (streak unevenness) containing streaks extending in the direction in which pixels are arranged may develop depending upon the imaging conditions under which a radiographic image is taken, and the linear unevenness (streak unevenness) thus developed varies according to the method used to read an electric signal corresponding to radiation received.

Further, when the line sensor has defective pixels, it produces streak unevenness in the scan direction as it scans and reads a radiographic image produced in the IP.

When using such an FPD or an IP to produce a radiographic image, there are cases where radiograph is achieved using a stationary grid having plates made of lead or another material that is impermeable to radiation and plates made of aluminum or another material that is permeable to radiation, alternately disposed therein, to prevent scatter light generated by a subject from entering an imaging medium. Use of such a stationary grid reduces generation of scatter light and thereby improves the contrast of a radiographic image but often causes the radiographic image to develop streak unevenness corresponding to edges of the lead plates used in the stationary grid.

Among methods of removing such streak unevenness from a radiographic image is one disclosed in JP 2003-150954 A filed by the Applicant of this application. According to this method, spatial frequency processing is performed using one-dimensional filters both in the same direction as that in which the streak unevenness (periodical pattern due to the stationary grid) extend and in the direction normal thereto to extract streak unevenness from the original image and subtract the streak unevenness from the original image, achieving removal of the streak unevenness from the original image.

For example, the original image is low-pass filtered one-dimensionally in the main scan direction, i.e., in the direction normal to the streak unevenness, to extract low-frequency components, which are then subtracted from the original image to extract high-frequency components, which in turn are subjected to one-dimensional low-pass filtering in the subscan direction to extract only the streak unevenness, which are then subtracted from the original image to remove the streak unevenness from the original image.

Thus, streak unevenness can be extracted and removed from the original image through the processing using a low-pass filter and a high-pass filter as described above.

However, filtering by a low-pass filter, etc. in the direction normal to the streak unevenness causes ringing in a region where a value of image data abruptly changes, such as at a streak, where the density greatly changes, or at the edge of an image.

Figure 4A:
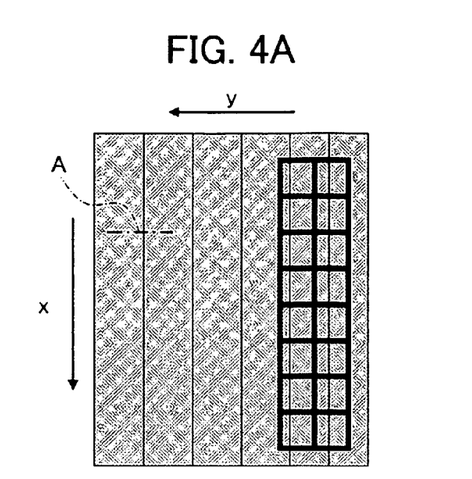
FIG. 4A illustrates a concept of a conventional method of removing streak unevenness.
Figure 4B:
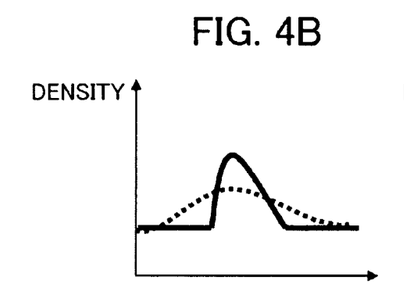
FIGS. 4B to 4E illustrate profiles in given regions, respectively.

For example, when an original image contains streak unevenness extending in the x direction as illustrated in FIG. 4A, a region A extending in the y direction normal to the streak unevenness and crossing one streak has a profile as indicated by a solid line in FIG. 4B.

Figure 4C:
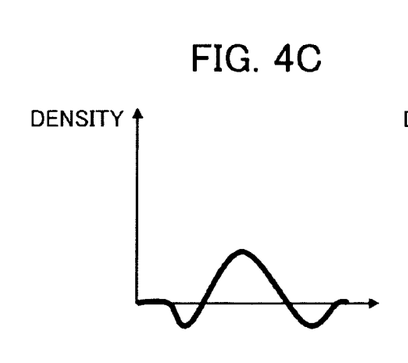

Low-pass filtering the region A in the y direction normal to the streak unevenness results in obtaining an image having a profile as indicated by the broken line in FIG. 4B. If the low-pass filtered image (broken line) is subtracted from the original image (solid line), ringing will result, as illustrated in FIG. 4C, such that the streak will have an abnormally low density at both ends thereof, where artifacts are produced.

Further, according to the method of extracting streak unevenness by processing the original image using an image processed by, for example, a low-pass filter, should a subject be parallel to the streak unevenness, the subject may also be detected as a streak unevenness, so that removal of streak unevenness may entail eliminating the necessary subject from the original image.

SUMMARY OF THE INVENTION

An object of the invention is to solve the above problems associated with the prior art and provide an image correction method and an image correction device for implementing the image correction method whereby streak unevenness observed in a radiographic image or various other images can be removed while restricting the occurrence of ringing sufficiently, and whereby a necessary subject of the image can be protected from removal.

An image correction method according to the invention comprises the steps of: median-processing the original image in a direction normal to a direction in which the streak unevenness extends to produce a median-processed image, subtracting the median-processed image from the original image to produce a subtraction image, threshold-processing a part of the subtraction image having a density exceeding a given threshold to reduce the density and produce a threshold-processed image, frequency-processing the threshold-processed image using a one-dimensional low-pass filter in the direction in which the streak unevenness extends to produce a processing image, and subtracting the processing image from the original image to remove the streak unevenness from the original image.

An image correction device according to the invention comprises: median processing means for median-processing an original image containing a streak unevenness in a direction normal to a direction in which the streak unevenness extends to produce a median-processed image, first subtraction means for subtracting the median-processed image from the original image to produce a subtraction image, threshold processing means for threshold-processing a part of the subtraction image where a density exceeds a given threshold to reduce the density and thus produce a threshold-processed image, filtering means for frequency-processing the threshold-processed image with a one-dimensional low-pass filter in the direction in which the streak unevenness extends to produce a filtered image, and second subtraction means for subtracting the filtered image from the original image.

DETAILED DESCRIPTION OF THE INVENTION

Now, the image correction method and the image correction device of the invention will be described in detail referring to preferred embodiments illustrated in the attached drawings.

Embodiment 1

Figure 1:
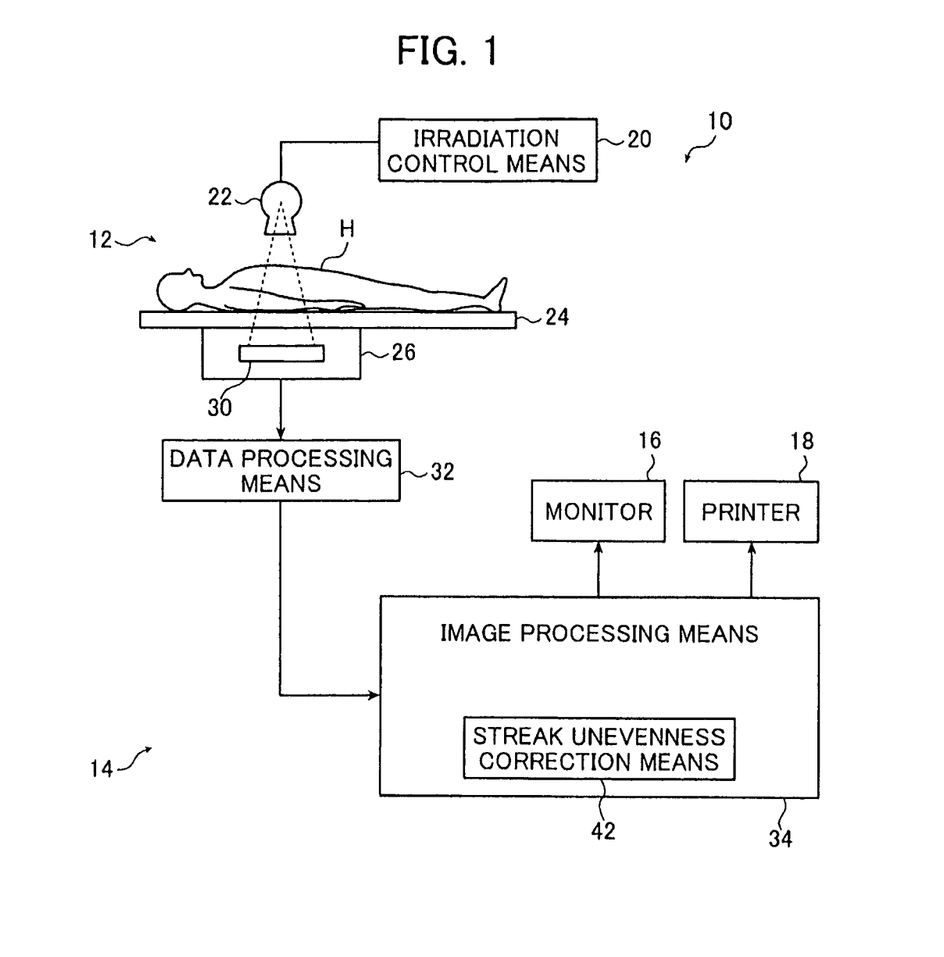
FIG. 1 illustrates a concept of an example of a radiographic imaging apparatus containing therein an image correction device according to an embodiment 1 of the invention.

FIG. 1 illustrates a configuration of a radiographic imaging apparatus 10 containing therein an image correction device according to an embodiment 1 of the invention.

The radiographic imaging apparatus 10 is a radiographic image diagnostic apparatus that produces a radiographic image of a subject H and comprises an imaging unit 12 for taking a radiographic image, an image processor 14 for processing an image of the subject taken by the imaging unit 12, a monitor 16, and a printer 18. The imaging apparatus 10 may be connected via a known communication network to external devices and systems such as a control system and an image server.

The imaging unit 12 takes a radiographic image of the subject H and comprises irradiation control means 20, a radiation source 22, a radiographic table 24, and imaging means 26.

The irradiation control means 20 is known control means for controlling the radiation source 22 and comprises a high-voltage power source for emitting radiation from the radiation source 22. The irradiation control means 20 operates the radiation source 22 to emit radiation having a given intensity for a given period of time. The radiation source 22 is a normal radiation source installed in various radiographic imaging apparatuses.

The radiographic table 24 is a normal radiographic table used for various radiographic imaging apparatuses. The imaging apparatus 10 may, where necessary, comprise moving means for moving the radiation source 22, another moving means for moving the radiographic table 24 vertically and horizontally, and tilting means for tilting the radiographic table 24.

The imaging means 26 produces a radiographic image of the subject H using a solid state radiation detector (FPD) 30.

As with a normal radiographic imaging apparatus, the imaging apparatus 10 receives radiation that was radiated by the radiation source 22 and penetrated the subject H with the light-receptive surface of the FPD 30 and performs photoelectric conversion on that radiation with the FPD 30 to produce an image of the subject H.

The FPD 30 is a normal flat panel detector used in various radiographic imaging apparatuses.

The FPD 30 may be any flat panel detector as appropriate according to the invention. The FPD 30 may be a direct-type FPD or a indirect-type FPD. A typical direct-type FPD, employing a photoconductive film such as one formed of amorphous selenium, collects and reads out electric charge, i.e., electron-hole pairs, generated by the photoconductive film in response to incident radiation as an electric signal. The indirect-type, employing a photo diode and a scintillator layer formed of a phosphor such as CsI:Tl that emits light in response to incident radiation, photoelectrically converts the light emitted by the scintillator layer in response to incident radiation into an electric signal and reads it out.

In the illustrated example of the imaging apparatus 10, the FPD 30 has, for example, TFTs (thin film transistors) disposed two-dimensionally for two-dimensionally arranged pixels and electrodes disposed in a direction corresponding to one of the directions in which the pixels are arranged so that the charges released from the photoconductive film to the pixels are allowed to flow in the read direction in which the electrodes are arranged and sequentially collected at the downstream ends.

Besides the FPD 30, the imaging means 26 may of course comprise other components, where necessary, with which known radiographic imaging apparatuses are equipped such as a grid for shielding scatter radiation that would otherwise enter the FPD 30 and means for moving the grid.

An output signal produced by the FPD 30 corresponding to the radiographic image is supplied to the image processor 14.

The image processor 14 processes the output signal of the FPD 30 to produce image data corresponding to the radiographic image for a monitor 16 to display an image, for a printer 18 to produce a print output, and further for use over a network and in recording media. The image processor 14 in the illustrated example of the imaging apparatus 10 comprises data processing means 32 and image processing means 34.

The image processor 14 may, for example, be configured by one or more computers and workstations and comprise where necessary other components than are illustrated, such as a keyboard and a mouse, to perform various operations including entering instructions.

The data processing means 32 performs given processing such as analog-to-digital conversion on the output signal of the FPD 30 to obtain image data of an image taken of the subject, which is supplied to the image processing means 34.

The image processing means 34 performs given image processing on the image data processed by the data processing means 32 and produces image data for the monitor 16 to display an image, for the printer 18 to produce a print output, and, further, for use over a network, in storage media, or other designated locations.

Thus, the image processing performed by the image processing means 34 is not limited specifically and may include all kinds of image processing performed by various radiographic imaging apparatuses and image processing apparatuses including gain correction (shading correction), offset correction, pixel defect correction, residual image correction, tone correction, density correction, and data conversion whereby image data is converted into data for a monitor to display or for a printer to print out. All these corrections may be performed by a known method.

The image processing means 34 further comprises streak unevenness correction means 42 for the inventive image correction device for implementing the inventive image correction method.

Figure 2:
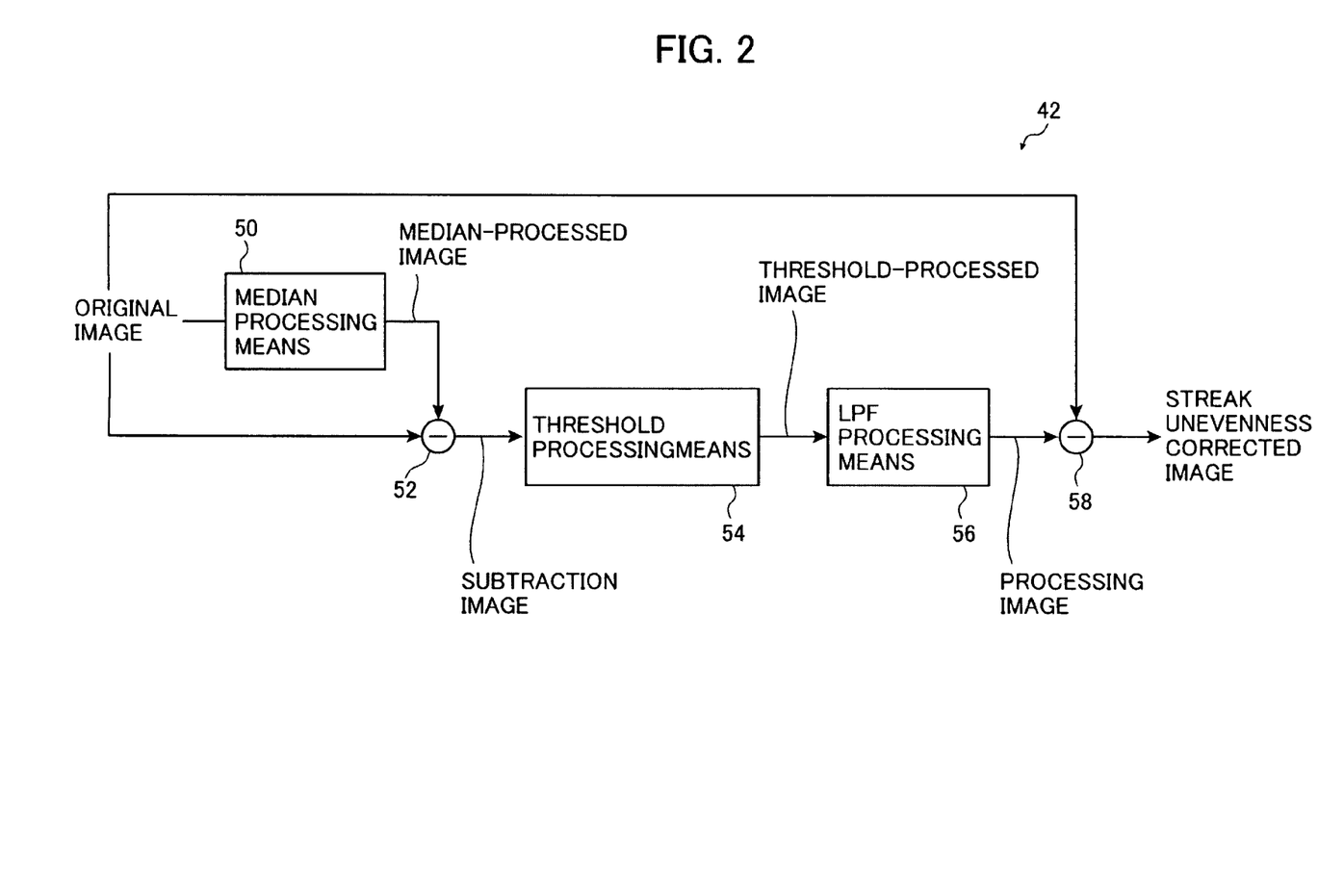
FIG. 2 is a block diagram illustrating a concept of an example of the image correction device according to the invention.

The streak unevenness correction means 42 removes streak unevenness linearly extending in a given direction in an image and comprises median processing means 50, first subtraction means 52, threshold processing means 54, LPF (low-pass filter) processing means 56, and second subtraction means 58, as illustrated in FIG. 2.

Now, the operations of removing streak unevenness performed by the streak unevenness correction means 42 will be described referring to FIGS. 2 and 3.

Figure 3A:
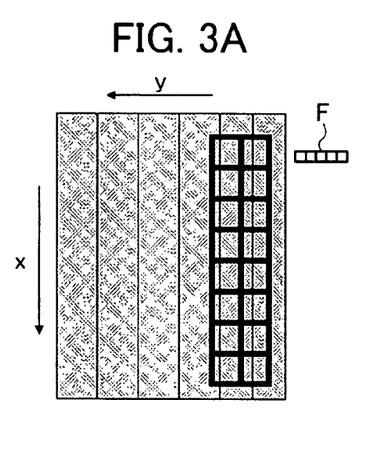
FIGS. 3A to 3E are views for explaining a concept of the method of removing streak unevenness according to the invention.

In the embodiment 1, an original image is produced by, for example, imaging a phantom having a lattice pattern formed by lines extending in the x-y directions in which pixels are arranged in the FPD 30 as shown by conceptual illustration in FIG. 3A. In the illustration, black thick lines represent the phantom, and the thin lines extending in the x direction represent the streak unevenness.

First, the median processing means 50 median-processes the original image.

The streak removal by the streak unevenness correction means 42 may be performed at any timing as appropriate that may be determined according to the kind of image processing executed by the image processing means 34, the order in which the steps of the processing are taken, and the like.

The median processing means 50 median-processes the original image in the direction normal to the direction in which the streak unevenness extend.

In the two-dimensional x-y pixel arrangements, the FPD 30 causes the electric charges released from the photoconductive films to flow in the x direction (read direction) and sequentially collects the electric charges at the downstream ends in the x direction to obtain electric charges released from the photoconductive film to the individual pixels.

The FPD 30, having such a configuration, may allow electric charges to leak from pixels depending upon the imaging conditions, where, for example, a large dose of radiation is used for radiography. The leaked electric charges are then allowed to flow in the x direction, i.e., the read direction, developing streak unevenness extending in the x direction. It is known that when the FPD 30 is used, the streak unevenness in the original image will, if produced, extend linearly in the x direction due to the structure of the FPD 30.

Therefore, the median processing means 50 performs median processing in the y direction, which is normal to the x direction in which electric charges are read.

Specifically, a filter F having a one-dimensional y-direction mask is moved relative to the original image in the y direction as illustrated in FIG. 3A to achieve median processing.

The size of the filter F for performing the median processing is not limited specifically: the filter F may have a size equivalent to any number of pixels as appropriate, which may be determined according to an assumed size of a streak of interest (the width of one streak=a number of pixels thereof in a direction normal to that in which they extend, i.e., a number of pixels in the y direction). The filter F preferably has a mask of a size equivalent to a number of pixels that is at least double an assumed size of the streak. The use of the filter F permits streak detection with an increased reliability.

Preferably, the filter F preferably has a mask of a size equivalent to an odd number of pixels to permit easy detection of a median, particularly a mask equivalent to $(2n+1)$ pixels where n is the number of pixels a streak of interest is assumed to contain in its width direction. As is known, median processing involves, for example, rearrangement of image data to detect a median, which leads to an increase in the data processing amount. However, the use of the film F having a mask equivalent to $(2n+1)$ pixels reduces the data processing amount to a minimum, expediting streak removal processing. With the FPD 30, where the electrodes are disposed in the read direction so that the electric charges released from the photoconductive film are allowed to flow in the read direction as in the illustrated example, a streak is typically assumed to have a size of a high-frequency streak, which is as small as several pixels, such that a small filter F suffices to extract the streak without regard to the calculation.

Figure 3B:
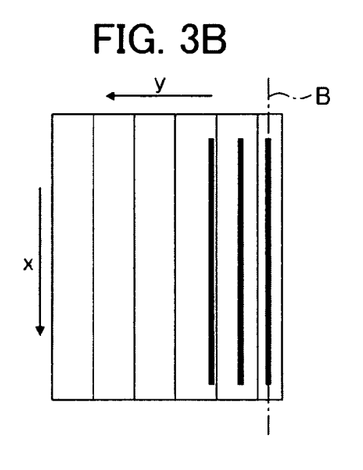

The median processing means 50 performs median processing in the y direction on the original image to produce a median-processed image, followed by subtraction performed by the first subtraction means 52 to subtract the median-processed image from the original image. The above process achieves extracting an image of lines extending in the x direction in the original image including the streak unevenness to produce a subtraction image as illustrated in FIG. 3B.

Conventionally, a one-dimensional low-pass filter that passes low-frequency pixels or a high-pass filter are used to perform frequency processing in directions normal to and parallel to the streak unevenness to remove streak unevenness as described by way of example in JP 2003-150954 A mentioned above.

However, in a region where the density changes abruptly as in a region A illustrated in FIG. 4A containing a streak where the density changes greatly, subtracting a low-pass filtered image from the original image will, as described above, cause ringing on both sides of the streak as illustrated in FIG. 4C, which in turn causes artifacts, etc. in an image from which such a streak has been removed.

Figure 4D:
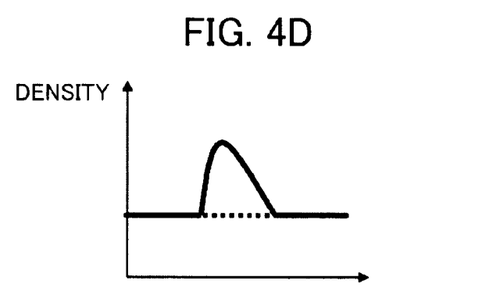
Figure 4E:
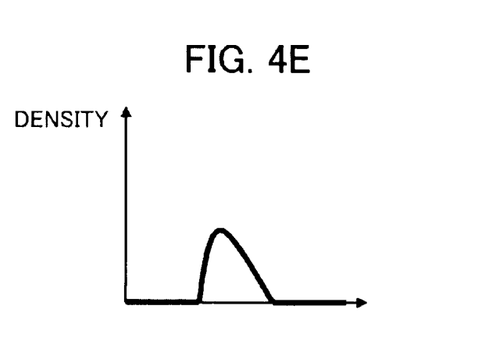

In contrast, according to the present invention wherein median processing is effected in the direction normal to a streak in lieu of processing with a low-pass filter, a median-processed image obtained by median-processing a region having a like profile exhibits a linear profile as illustrated in broken line in FIG. 4D. Accordingly, subtraction of a median-processed image from an original image still permits restriction of occurrence of ringing as illustrated in FIG. 4E and therefore permits optimal restriction of occurrence of artifacts caused by ringing in an image from which streak unevenness have been removed.

The subtraction image obtained by the first subtraction means 52 is then processed by the threshold processing means 54.

The threshold processing means 54 extracts a pixel exceeding a given density threshold from the subtraction image and threshold-processes the pixel to reduce the density of that pixel. Preferably, the threshold processing sets the density of a pixel exceeding a given threshold to "0 (minimum density)." FIG. 3C illustrates a threshold-processed image obtained in this manner.

Thus, the threshold processing by the threshold processing means 54 extracts a region in the subtraction image where the density exceeds a given threshold as a subject and reduces the density of the subject, preferably to "0."

There is no limitation to the method of reducing the density of a pixel exceeding a given threshold. An alternative method of reducing the density of a pixel exceeding a given threshold, for example, is to copy and use the density of a pixel not exceeding the threshold and located on the same line on which that pixel lies.

Figure 3C:
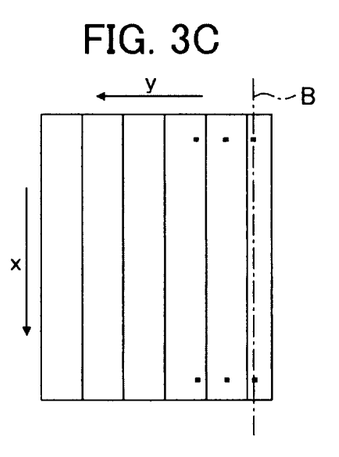
Figure 5A:
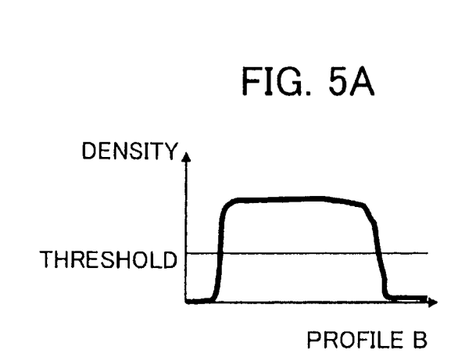
FIGS. 5A and 5B illustrate profiles of a region B corresponding to FIGS. 3B and 3C, respectively.
Figure 5B:
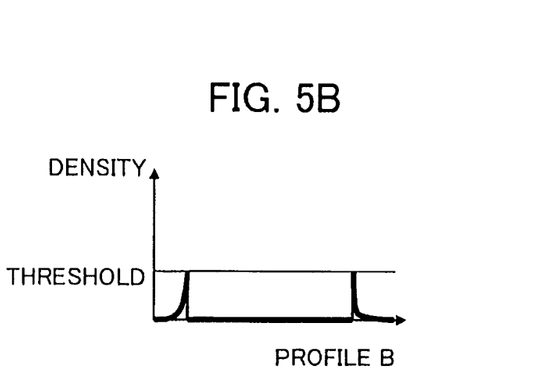

Suppose that a region B extending in the x direction of a subtraction image as illustrated in FIG. 3B has a profile of FIG. 5A, when threshold processing is performed to reduce a pixel density exceeding a threshold to "0," the threshold-processed region B will acquire a profile as illustrated in FIG. 5B, thus obtaining a threshold-processed image from which a high density region has been removed as illustrated in FIG. 3C.

A linear subject extending in the same direction as the streak unevenness may remain in the subtraction image obtained by subtracting the median-processed image from the original image.

According to the invention, the threshold-processed image is subsequently low-pass filtered as will be described to remove a subject that is short in the x direction, etc. thereby to extract a streak, which is subtracted from the original image to remove the streak from the original image. Should low-pass filtering be performed without threshold processing, a linear subject extending in the same direction as streak unevenness would also be extracted as streak, with the result that a necessary subject is also removed from the original image.

According to the invention, however, when a region has a density exceeding a given threshold, the density is reduced, preferably to "0." This restrains extraction of a subject from an original image as streak and enables streak removal with a higher accuracy.

In a typical radiographic image taken using a solid-state) image sensing device such as the FPD 30, the density of a streak resulting from saturation of built-up pixel charges reached after exceeding a limit or other conditions is typically lower than that of the subject in the original image although it may vary with imaging conditions such as dose of radiation, temperature of the FPD 30, etc.

Thus, there is a degree of difference in density between subject and streak, and setting a threshold between them enables removal of the linear subject extending in a threshold-processed image in the same direction as streak unevenness.

There is no specific limitation to the method of setting the threshold; the threshold may be determined as appropriate, for example, by conducting an experiment or simulation. For example, an experiment or simulation may be conducted using a phantom under various imaging conditions to select and set an appropriate density for removing streak unevenness without removing the subject.

According to the invention, the threshold used for the threshold processing may be varied as appropriate according to the imaging conditions (tube voltage, exposure period, dose of radiation, etc.), imaged location, temperature of the FPD 30, time elapsed from the last radiograph, and the like.

Two or more thresholds may be provided in the imaging apparatus 10 to permit selection of an optimal one for threshold processing according to imaging conditions, imaged location, etc.

Then, the threshold-processed image obtained by the threshold processing means 54 is then processed by the LPF processing means 56.

The LPF processing means 56 uses a one-dimensional low pass filter extending in the y direction normal to the direction in which the streak unevenness extend (low pass filter for extracting only low-frequency spatial-frequency components) to perform processing in the x direction, in which the streak unevenness extend, and extract a region extending in the x direction as streak unevenness.

Figure 3D:
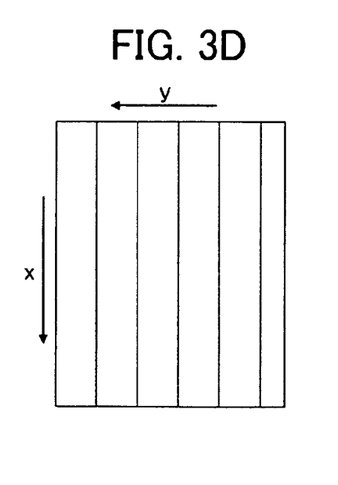

Thus, a subject, etc. short in the x direction is removed from the threshold-processed image as illustrated in FIG. 3C to produce a processing image as illustrated in FIG. 3D obtained by extracting only the streak unevenness from the original image.

When its cutoff frequency is too high, the low-pass filter used in the LPF processing means 56 may extract a short subject that should not be extracted as streak; when its cutoff frequency is too low, the low-pass filter is unable to extract a streak that should be extracted as streak. The characteristics of the low-pass filter may be selected/set as appropriate so that streak unevenness may be removed but the subject is not extracted by, for example, conducting an experiment or simulation using a phantom, etc. under various imaging conditions.

Figure 3E:
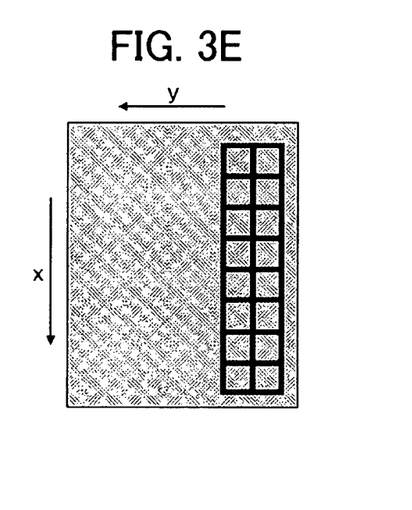

Upon producing the processing image as described above, the processing image is subtracted from the original image by the second subtraction means 58 to finally produce a streak unevenness-corrected image where the streak unevenness have been removed from the original image as illustrated in FIG. 3E.

As is apparent from the above, the median processing is first performed in the direction normal to the streak unevenness, which restricts occurrence of ringing in streak unevenness where the density greatly changes, edges of the subject, and other regions where the density changes abruptly and thus restricts occurrence of artifacts, etc. caused by ringing, thereby to achieve removal of the streak unevenness from the original image.

Further, threshold processing performed on the subtraction image obtained by subtracting the median-processed image from the original image to reduce the density of a region (pixel or pixels) exceeding a threshold, preferably to "0," restrains extraction of the subject extending in the same direction as the streak unevenness in the original image and appropriately prevents removal of the necessary subject in streak removal processing.

Thus, the radiographic image on which a given image processing has been performed including streak removal by the image processing means 34 is supplied to the monitor 16 and thereby displayed as visible image, supplied to the printer 18 and thereby produced as hard copy, or supplied to other designated locations via network.

The above examples illustrate applications of the present invention to removal of streak unevenness from a radiographic image produced by the FPD 30. However, the invention is not limited thereto and may be applied to various images where streak unevenness, when developed, extend in a known direction.

With a type of scanner using a line sensor such as a line CCD sensor having reader pixels arranged in one direction and a linear light source extending in the same direction as the line sensor to read an image by scanning the image with the line sensor and the linear light source in the direction normal to the direction in which the line sensor's reader pixels are arranged, when defective pixels develop in the line sensor, they produce streak unevenness in the scan direction (the direction in which the line sensor and the image to be read move relative to each other). Variation in light amount even in a part of the linear light source may also cause streak unevenness extending in the scan direction.

Therefore, where the original image is an image obtained with such a scanner, median processing can be appropriately performed in the direction normal to the scan direction.

Further, there is known a radiographic image reading apparatus, such as FCR referred to earlier, that uses reading means comprising a like line sensor and a linear exciter light source formed of LEDs arrayed in the same direction as the line sensor, wherein the linear exciter light source radiates exciter light in the direction normal to the direction in which the line sensor extends as the reading means scans the radiographic image conversion panel (IP) to read a radiographic image produced on the IP by the line sensor.

That radiographic image reading apparatus is liable to develop streak unevenness extending in the scan direction when the line sensor has developed defective pixels or when the linear exciter light source has developed defects such as luminance failure at a spot in the linear exciter light source.

Therefore, where the original image is a radiographic image obtained through such a radiographic image reading apparatus, median processing can likewise be appropriately performed in the direction normal to the scan direction.

In the case of a radiographic image taken using a stationary grid as described in JP 2003-150954 A referred to earlier, wherein streak unevenness extending in the direction in which the grid lies periodically develop in the direction normal to the streak unevenness, median processing means 50 can appropriately perform median processing in the direction normal to the direction in which the grid lies.

Further, it is known that a CCD sensor used in, for example, a digital camera and having two-dimensionally arranged pixels develop a streak like a whiteout or a so-called smear in the vertical direction (in the charge transfer direction) when such a high dose of light is radiated that the pixel charge buildup exceeds a limit. Therefore, where the original image is an image produced by such a CCD sensor, median processing can be appropriately performed in the direction normal to the vertical direction (in the charge transfer direction) in the CCD.

While the image correction method and the image correction device of the invention has been described in detail, various changes and modifications may be made without departing from the true spirit and scope of the invention.

The present invention can be suitably used for image processing of an image produced by a radiographic imaging apparatus, a scanner and an imaging device using a CCD sensor (line/area), and the like and for these apparatuses and devices.

What is claimed is:

1. An image correction method for removing a streak unevenness from an original image, the method comprising:
   median-processing the original image in a direction normal to a direction in which the streak unevenness extends to produce a median-processed image,
   subtracting the median-processed image from the original image to produce a subtraction image,
   threshold-processing a part of the subtraction image having a density exceeding a given threshold to reduce the density and produce a threshold-processed image,
   frequency-processing the threshold-processed image using a one-dimensional low-pass filter in the direction in which the streak unevenness extends to produce a processing image, and
   subtracting the processing image from the original image to remove the streak unevenness from the original image,
   wherein the given threshold is set between the density of a subject extending in the same direction as the streak unevenness and the density of the streak unevenness.

2. The image correction method according to claim 1, wherein the median processing uses a one-dimensional filter having a mask of a size equivalent to at least double a number of pixels of the streak unevenness in a direction normal to the direction in which the streak unevenness extends.

3. The image correction method according to claim 2, wherein the mask of the filter has a size equivalent to an odd number of pixels.

4. The image correction method according to claim 3, wherein the filter has a mask of a size equivalent to (2n+1) pixels for n pixels of the streak unevenness in the direction normal to the direction in which the streak unevenness extends.

5. The image correction method according to claim 1, wherein the original image is an image obtained with an image sensing device for reading a signal in one of directions in which pixels are arrayed two-dimensionally, and wherein the median processing is performed in a direction normal to a direction in which the signal is read.

6. The image correction method according to claim 1, wherein the original image is an image read by a line sensor comprising reader pixels arranged in one direction by scanning an object to be read with the line sensor in a direction normal to the direction in which the reader pixels are arranged, and wherein the median processing is performed in a direction normal to the direction of the scanning of the object to be read with the line sensor.

7. The image correction method according to claim 1, wherein the original image is a radiographic image obtained through a stationary grid, and wherein the median processing is performed in a direction normal to a direction in which the grid extends.

8. An image correction device comprising:
   a median processing unit that median-processes an original image containing a subject and a streak unevenness in a direction normal to a direction in which the streak unevenness extends to produce a median-processed image,
   a first subtraction for unit that subtracts the median-processed image from the original image to produce a subtraction image,
   a threshold processing unit that threshold-processes a part of the subtraction image where a density exceeds a given threshold to reduce the density and thus produce a threshold-processed image,
   a filtering unit that frequency-processes the threshold-processed image with a one-dimensional low-pass filter in the direction in which the streak unevenness extends to produce a filtered image, and
   a second subtraction unit that subtracts the filtered image from the original image,
   wherein the given threshold is set between the density of a subject extending in the same direction as the streak unevenness and the density of the streak unevenness.

9. The image correction device according to claim 8, wherein the median processing unit processes the original image using a one-dimensional filter having a mask of a size equivalent to at least double a number of pixels for pixels of the streak unevenness in the direction normal to the direction in which the streak unevenness extends.

10. The image correction device according to claim 9, wherein the mask of the filter has a size equivalent to an odd number of pixels.

11. The image correction device according to claim 10, wherein the filter has a mask of a size equivalent to (2n+1) pixels for n pixels of the streak unevenness in the direction normal to the direction in which the streak unevenness extends.

12. The image correction device according to claim 8, wherein the original image is an image obtained with an image sensing device for reading a signal in one of directions in which pixels are arrayed two-dimensionally, and wherein the median processing unit performs median processing in a direction normal to a direction in which the signal is read.

13. The image correction device according to claim 8, wherein the original image is an image read by a line sensor comprising reader pixels arranged in one direction by scanning an object to be read with the line sensor in a direction normal to the direction in which the reader pixels are arranged, and wherein the median processing unit performs median processing in a direction normal to the direction of the scanning of the object to be read with the line sensor.

14. The image correction device according to claim 8, wherein the original image is a radiographic image obtained through a stationary grid, and wherein the median processing unit performs median processing in a direction normal to a direction in which the grid extends.

* * * * *